(12) United States Patent
Casper et al.

(10) Patent No.: US 12,090,257 B2
(45) Date of Patent: Sep. 17, 2024

(54) BLOOD MONITORING SYSTEM FOR DETECTING OCCULT HEMORRHAGES

(71) Applicants: Fresenius Medical Care Holdings, Inc., Waltham, MA (US); Fresenius Medical Care Deutschland GmbH, Bad Homburg (DE)

(72) Inventors: Sabrina Casper, Bad Homburg (DE); Peter Kotanko, New York, NY (US)

(73) Assignees: Fresenius Medical Care Deutschland GmbH, Bad Homburg (DE); Fresenius Medical Care Holdings, Inc., Waltham, MA (US)

( * ) Notice: Subject to any disclaimer, the term of this patent is extended or adjusted under 35 U.S.C. 154(b) by 365 days.

(21) Appl. No.: 17/132,710

(22) Filed: Dec. 23, 2020

(65) Prior Publication Data

US 2022/0193320 A1   Jun. 23, 2022

(51) Int. Cl.
*A61M 1/16* (2006.01)
*A61M 1/36* (2006.01)

(52) U.S. Cl.
CPC ........ *A61M 1/1603* (2014.02); *A61M 1/3609* (2014.02); *A61M 2205/18* (2013.01); *A61M 2230/207* (2013.01)

(58) Field of Classification Search
None
See application file for complete search history.

(56) References Cited

U.S. PATENT DOCUMENTS

| | | | |
|---|---|---|---|
| 6,006,119 A * | 12/1999 | Soller | A61B 5/14552 356/39 |
| 9,801,993 B2 | 10/2017 | Barrett et al. | |
| 2011/0205535 A1* | 8/2011 | Soller | A61B 5/1455 356/300 |
| 2016/0038042 A1 | 2/2016 | Mulligan et al. | |
| 2018/0372757 A1 | 12/2018 | Macintyre et al. | |
| 2019/0008427 A1* | 1/2019 | Satish | A61B 5/4875 |
| 2020/0297259 A1* | 9/2020 | Feldschuh | A61B 5/02042 |

OTHER PUBLICATIONS

"A Blood Circulation Model for Reference Man", Leggett et al., received Dec. 4, 1996, 17 total pages. (Year: 1996).*

(Continued)

*Primary Examiner* — Jonathan M Peo
(74) *Attorney, Agent, or Firm* — Leydig, Voit & Mayer, Ltd.

(57) ABSTRACT

A method for detecting occult hemorrhages is provided. The method includes obtaining a first hematocrit concentration prior to infusing a saline solution into a bloodstream of a patient. The method further includes infusing the saline solution into the bloodstream of the patient and obtaining a second hematocrit concentration after infusing the saline solution into the bloodstream. The method also includes determining a first absolute blood volume based on the first hematocrit concentration and the second hematocrit concentration. In addition, the method includes generating a notification indicating a potential occult hemorrhage based on the first absolute blood volume and a pre-defined absolute blood volume threshold, and providing the notification indicating the potential occult hemorrhage.

10 Claims, 6 Drawing Sheets

(56) References Cited

OTHER PUBLICATIONS

Chu et al., "Incidence and risk factors of gastrointestinal bleeding in mechanically ventilated patients," *World J. Emerg. Med*, 1(1), 2010.
Shahi et al., "Using Serial Hemoglobin Levels to Detect Occult Blood Loss in the Early Evaluation of Blunt Trauma Patients," *Journal of Emergency Medicine*, 55 (3) (2018).
International Patent Application No. PCT/US2021/060664, Search Report (Mar. 15, 2022).

* cited by examiner

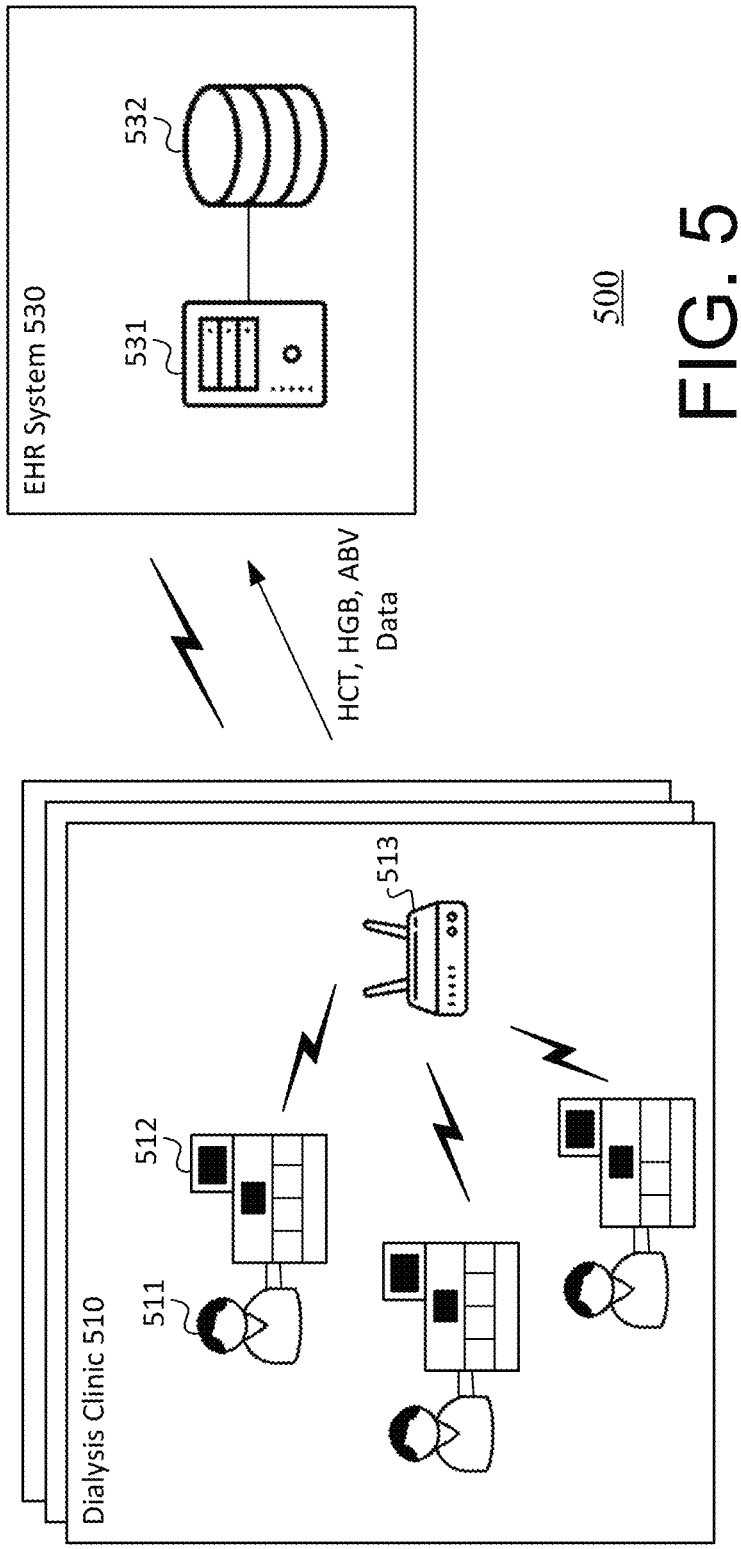

BLOOD MONITORING SYSTEM FOR DETECTING OCCULT HEMORRHAGES

BACKGROUND

Patients in intensive care units (ICUs) may suffer from occult hemorrhages, including dialysis patients in ICUs. Occult hemorrhages may occur, for example, in gastrointestinal (GI) tracts, soft tissues, body cavities, and/or other locations. The longer an occult hemorrhage is left undetected, the more serious the health implications become for the patient. In its initial stages, since both corpuscular blood elements (mostly red blood cells (RBCs) and plasma are lost in equal proportion, occult hemorrhages are sometimes difficult to detect. The methods and systems disclosed herein are directed to overcoming the difficulty in detecting occult hemorrhages for certain patients.

SUMMARY

In an exemplary embodiment, the present application provides a method for detecting occult hemorrhages. The method comprises: obtaining, by a medical system comprising a blood monitoring system, a first hematocrit concentration prior to infusing a saline solution into a bloodstream of the patient; infusing, by the medical system, the saline solution into the bloodstream of the patient; obtaining, by the medical system, a second hematocrit concentration after infusing the saline solution into the bloodstream; determining, by the medical system, a first absolute blood volume based on the first hematocrit concentration and the second hematocrit concentration; generating, by the medical system, a notification indicating a potential occult hemorrhage based on the first absolute blood volume and a pre-defined absolute blood volume threshold; and providing, by the medical system, the notification indicating the potential occult hemorrhage.

In another exemplary embodiment, the present application provides another method for detecting occult hemorrhages. The method comprises: monitoring, by a blood monitoring system of a medical system, hematocrit or hemoglobin concentrations corresponding to blood of the patient over a period of time; based on the monitoring, comparing, by the blood monitoring system, a detected hematocrit concentration or a hemoglobin concentration with a pre-defined threshold; in response to the detected hematocrit concentration or the hemoglobin concentration exceeding the pre-defined threshold, generating, by the blood monitoring system, a notification indicating a potential occult hemorrhage; and providing, by the blood monitoring system, the notification indicating the potential occult hemorrhage.

In yet another exemplary embodiment, the present application provides a medical system comprising a blood monitoring system, one or more processors, and a non-transitory computer-readable medium having processor-executable instructions stored thereon. The processor-executable instructions, when executed by the one or more processors, facilitate: monitoring a hematocrit concentration or a hemoglobin concentration corresponding to the blood of the patient over a period of time; generating a notification indicating a potential occult hemorrhage based on a change of the hematocrit concentration or the hemoglobin concentration; and providing the notification indicating the potential occult hemorrhage.

BRIEF DESCRIPTION OF THE DRAWINGS

FIG. 5 is a block diagram of an exemplary network environment in which a hemodialysis system communicates with an electronic health records (EHR) system to provide data to the EHR system.

DETAILED DESCRIPTION

Exemplary embodiments of the present application provide for early detection of occult hemorrhages based on measurements of hematocrit values, hemoglobin levels, and/or absolute volumes. Although in the initial stages an occult hemorrhage is difficult to detect, following this initial period there is a drop in a patient's hematocrit and hemoglobin concentrations due to the re-distribution of interstitial fluid into the vascular bed as corpuscular blood elements are lost, and this drop is detectable through continuous or periodic monitoring of the patient's blood via a blood monitoring system in accordance with certain exemplary embodiments. Additionally, in other exemplary embodiments, repeated measurements of absolute blood volume (ABV) may be performed in connection with a fluid infusion for detection of an occult hemorrhage.

Based on these measurements of hematocrit, hemoglobin, and/or ABV, exemplary embodiments of the present application are able to achieve relatively early detection of an occult hemorrhage within a patient, which provides for a greater likelihood the patient is able to be treated in a timely manner.

Based on the aforementioned measurements, a blood monitoring system may provide a notification indicating a potential occult hemorrhage. Additionally, and/or alternatively, a fluid (e.g., saline) may be infused into the patient using a timed pump. Based on the infusion, the blood monitoring system may continuously or periodically measure the hematocrit or hemoglobin values of the patient and use the measured values to determine changes in absolute blood volumes. The blood monitoring system may then use the changes in absolute blood volumes to determine whether the patient is potentially suffering from an occult hemorrhage.

Figure 1:
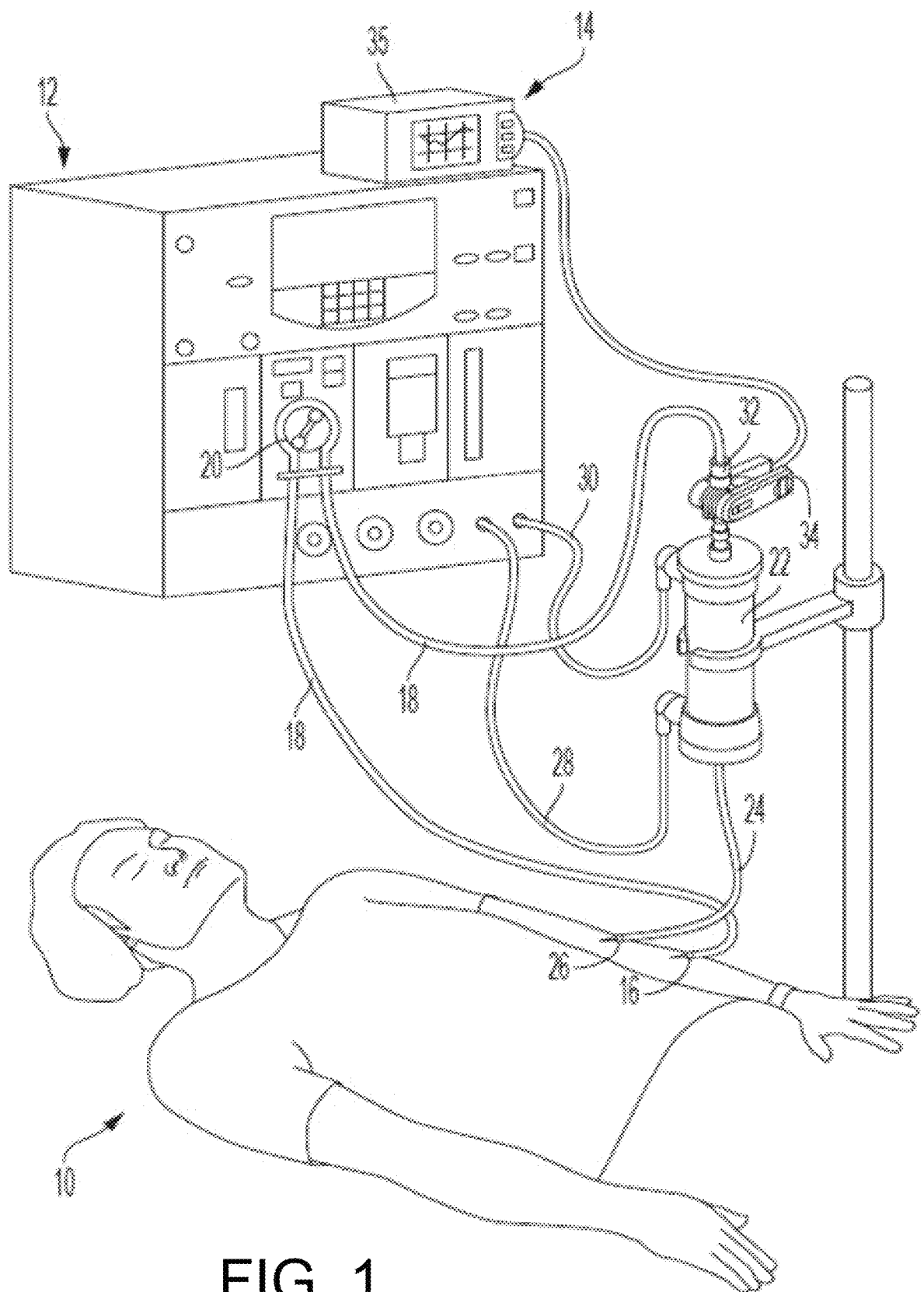
FIG. 1 is a schematic diagram of an exemplary medical treatment system having an optical blood monitoring system.

FIG. 1 is a schematic diagram of an exemplary medical system having an optical blood monitoring system. By way of example, the medical system shown in FIG. 1 is a hemodialysis system; however, other extracorporeal medical systems having an optical blood monitoring system are contemplated or blood monitoring systems configured for standalone use or use with a variety of medical systems are contemplated. The hemodialysis system may be used to measure/determine hematocrit (HCT), hemoglobin (HGB), and/or absolute blood volumes (ABV) of a patient 10. The hemodialysis system may use the measurements/determinations to determine whether the patient 10 is suffering from an occult hemorrhage (OH). For example, FIG. 1 depicts a patient 10 undergoing hemodialysis treatment using a hemodialysis machine 12. The hemodialysis system further includes an optical blood monitoring system 14.

An inlet needle or catheter 16 is inserted into an access site of the patient 10, such as in the arm, and is connected to extracorporeal tubing 18 that leads to a peristaltic pump 20 and to a dialyzer 22 (or blood filter). The dialyzer 22 removes toxins and excess fluid from the patient's blood. The dialyzed blood is returned from the dialyzer 22 through extracorporeal tubing 24 and return needle or catheter 26. In some parts of the world, the extracorporeal blood flow may additionally receive a heparin drip to prevent clotting. The excess fluids and toxins are removed by clean dialysate liquid which is supplied to the dialyzer 22 via tube 28, and waste liquid is removed for disposal via tube 30. A typical hemodialysis treatment session takes about 3 to 5 hours in the United States. Additionally, and/or alternatively, patients in ICUs may also undergo hemodialysis treatments and/or other dialysis/blood monitoring treatments.

The optical blood monitoring system 14 includes a display device 35 and a sensor device 34. The sensor device 34 may, for example, be a sensor clip assembly that is clipped to a blood chamber 32, wherein the blood chamber 32 is disposed in the extracorporeal blood circuit. A controller (e.g., processor) of the optical blood monitoring system 14 may be implemented in the display device 35 or in the sensor clip assembly 34, or both the display device 35 and the sensor clip assembly 34 may include a respective controller for carrying out respective operations associated with the optical blood monitoring system.

The blood chamber 32 may be disposed in line with the extracorporeal tubing 18 upstream of the dialyzer 22. Blood from the peristaltic pump 20 flows through the tubing 18 into the blood chamber 32. The sensor device 34 includes emitters that emit light at certain wavelengths and detectors for receiving the emitted light after it has passed through the blood chamber 32. For example, the emitters may include LED emitters that emit light at approximately 810 nm, which is isobestic for red blood cells, at approximately 1300 nm, which is isobestic for water, and at approximately 660 nm, which is sensitive for oxygenated hemoglobin, and the detectors may include a silicon photodetector for detecting light at the approximately 660 and 810 nm wavelengths, and an indium gallium arsenide photodetector for detecting light at the approximately 1300 nm wavelength. The blood chamber 32 includes lenses or viewing windows that allows the light to pass through the blood chamber 32 and the blood flowing therein.

An example of an optical blood monitoring system having a sensor clip assembly configured to measure hematocrit and oxygen saturation of extracorporeal blood flowing through a blood chamber is described in U.S. Pat. No. 9,801,993, titled "SENSOR CLIP ASSEMBLY FOR AN OPTICAL MONITORING SYSTEM," which is incorporated by reference in its entirety herein.

A controller of the optical blood monitoring system 14 uses the light intensities measured by the detectors to determine HCT values for blood flowing through the blood chamber 32. The controller calculates HCT, HGB, oxygen saturation, and change in blood volume (e.g., ABV) associated with blood passing through the blood chamber 32 to which the sensor device 34 is attached using a ratiometric model. The intensity of the received light at each of the various wavelengths is reduced by attenuation and scattering from the fixed intensity of the visible and infrared light emitted from each of the LED emitters. Beer's Law, for each wavelength of light, describes attenuation and scattering as follows:

$$i_n = I_{0-n} * e^{-\varepsilon_p X_p d_{pt}} * e^{-\varepsilon_b X_b d_b} * e^{-\varepsilon_p X_p d_{pr}} \qquad \text{Eq. (1)}$$

where $i_n$=received light intensity at wavelength n after attenuation and scattering; $I_{0-n}$=transmitted light intensity at wavelength n incident to the measured medium; e=the natural exponential term; ε=the extinction coefficient for the measured medium (p—blood chamber polycarbonate, b—blood); X=the molar concentration of the measured medium (p—blood chamber polycarbonate, b—blood); and d=the distance through the measured medium (pt—transmitting blood chamber polycarbonate, b—blood, pr—receiving blood chamber polycarbonate).

Since the properties of the polycarbonate blood chamber do not change, the first and third exponential terms in the above Eq. (1) are constants for each wavelength. Mathematically, these constant terms are multiplicative with the initial constant term $I_{0-n}$ which represents the fixed intensity of the radiation transmitted from a respective LED emitter. For simplification purposes, Eq. (1) can be rewritten in the following form using bulk extinction coefficients and a modified initial constant $I'_{0-n}$ as follows:

$$i_n = I'_{0-n} * e^{-\alpha d} \qquad \text{Eq. (2)}$$

where $i_n$=received light intensity at wavelength "n" after attenuation and scattering as though the detector were at the receive blood boundary; α=the bulk extinction coefficient ($\alpha_b = \varepsilon_b X_b$) and $I'_{0-n}$=the equivalent transmitted light intensity at wavelength n as if applied to the transmit blood boundary accounting for losses through the blood chamber. Note that the term $I'_{0-n}$ is the light intensity incident on the blood with the blood chamber losses included.

Using the approach defined in Eq. (2) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values a for the red blood cells and the water constituents in the blood chamber, respectively. A mathematical function than defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \qquad \text{Eq. (3)}$$

where $i_{810}$ is the light intensity of the photo receiver at 810 nm, $i_{1300}$ is the infrared intensity of the photodetector at 1300 nm and $I_{0-810}$ and $I_{0-1300}$ are constants representing the intensity incident on the blood accounting for losses through the blood chamber. The above equation holds true assuming that the flow of blood through the blood chamber 32 is in steady state, i.e. steady pressure and steady flow rate.

The preferred function f[ ] is a second order polynomial having the following form:

$$HCT = f\left[\frac{\ln\left(\frac{i_{810}}{I_{0-810}}\right)}{\ln\left(\frac{i_{1300}}{I_{0-1300}}\right)}\right] = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C. \qquad \text{Eq. (4)}$$

A second order polynomial is normally adequate as long as the infrared radiation incident at the first and second wavelengths is substantially isobestic.

After the HCT value has been determined by a controller at the sensor device 34 or at the display device 35, the display device may be used to output the determined HCT value. Further, the controller may further determine an HGB concentration value based on the determined HCT value, with the HGB concentration value also being output on the display device 35.

For instance, the HGB for a blood sample corresponds to the mass of protein (e.g., in grams) for the blood sample, and an HGB concentration value corresponds to a protein mass per unit of blood sample volume. The HGB concentration value may be determined based on multiplying an HCT value and a mean corpuscular hemoglobin concentration (MCHC) value. It will be appreciated that the HCT value corresponds to the volume of red blood cells (RBCs) in a blood sample divided by the total volume of the blood sample, and that the MCHC value corresponds to an average mass of HGB per RBC divided by an average volume per RBC. It will further be appreciated that the MCHC value corresponds to mean corpuscular hemoglobin (MCH) divided by mean corpuscular volume (MCV), wherein MCH corresponds to an average mass of HGB per RBC of a patient (e.g., in picograms), and wherein MCV corresponds to an average volume per RBC of a patient (e.g., in femtoliters). Thus, when the HCT value is multiplied by the MCHC value, the HGB concentration value that is determined corresponds to a protein mass per unit of blood sample volume.

The hemodialysis system depicted in FIG. 1 may be one of a plurality of hemodialysis systems in a dialysis clinic and/or in ICUs. Patients may come into the dialysis clinic for treatments at regular intervals, for example, on a Monday-Wednesday-Friday schedule or a Tuesday-Thursday-Saturday schedule. Additionally, and/or alternatively, patients may be connected to hemodialysis systems in ICUs if necessary.

It will be appreciated that the hemodialysis system depicted in FIG. 1 is merely exemplary. The principles discussed herein may be applicable to other medical systems in which blood monitoring operations are performed.

Figure 2:
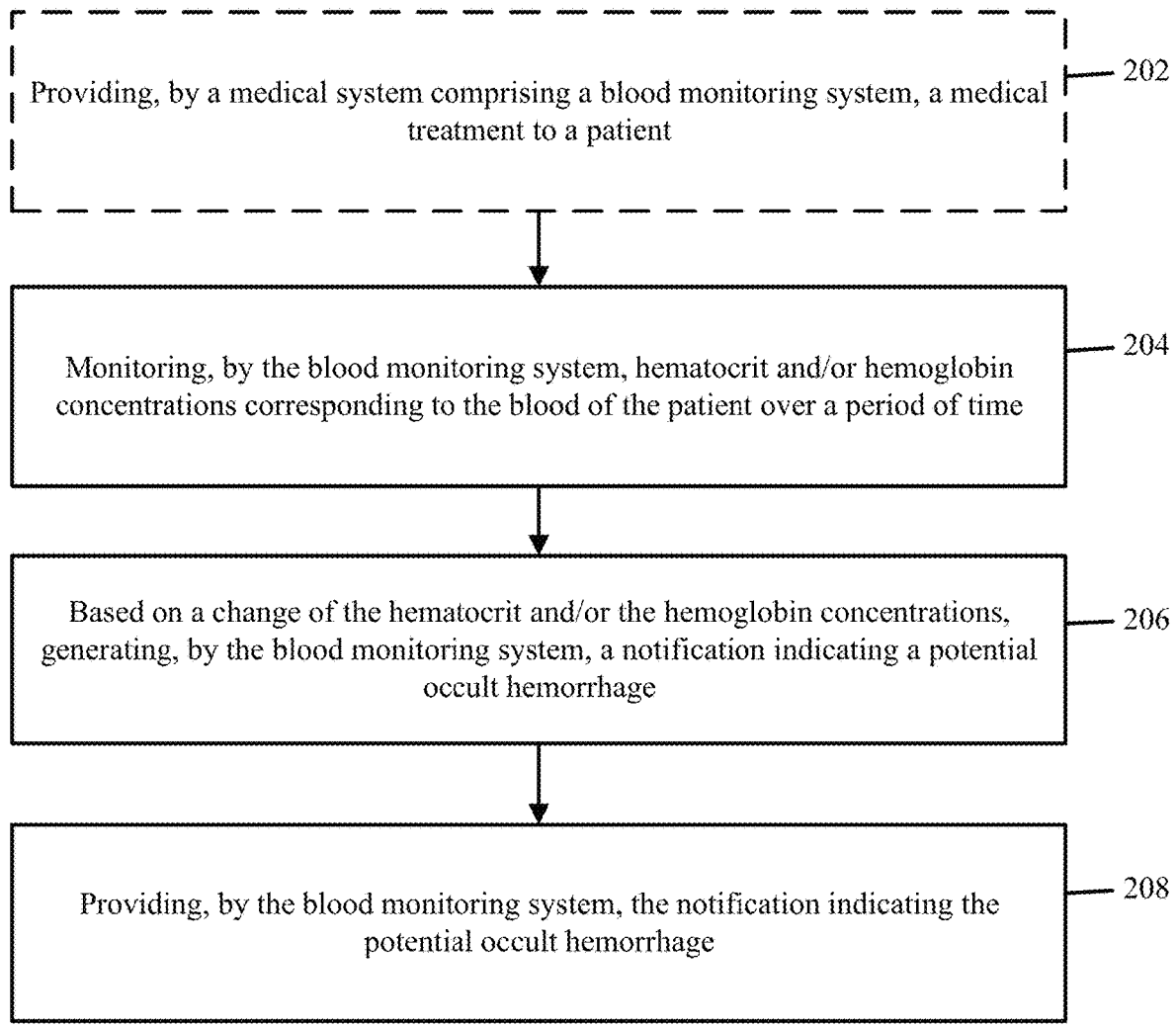
FIG. 2 is a flowchart of an exemplary process for detecting occult hemorrhages.

FIG. 2 is a flowchart of an exemplary process 200 for detecting occult hemorrhages. The process 200 may be performed by any type of medical system comprising a blood monitoring system. In some instances, the medical system may be the dialysis system described in FIG. 1. For instance, as described above, the dialysis system may perform dialysis treatments and may comprise a blood monitoring system 14 and a dialysis machine 12. The dialysis system may perform the blocks 202-208 of process 200. In other instances, the medical system that performs process 200 may be a medical system that performs additional and/or alternative medical treatments. Additionally, and/or alternatively, the medical system that performs 200 may include a blood monitoring system that is configured to obtain transcutaneous and/or non-invasive blood measurements such as transcutaneous measurements of HGB and/or HCT.

At block 202, a medical system (e.g., the hemodialysis system discussed above in connection with FIG. 1) provides a medical treatment to a patient (e.g., the patient 10). The medical system comprises a blood monitoring system. For example, the patient 10 may be connected to a blood monitoring system for a variety of reasons and in numerous different circumstances. In some instances, the patient 10 may be admitted to an ICU and a physician or clinician may connect to the patient 10 to a blood monitoring system. As mentioned above, patients in ICUs may suffer from OHs (especially in GI tracts, soft tissues, and body cavities) and detecting these OHs in a timely manner is very beneficial with regard to preventing negative outcomes for such patients.

In some examples, at block 202, the blood monitoring system provides dialysis treatment for the patient 10 and the dialysis treatment comprises circulating blood of the patient through a blood circuit.

In some variations and as denoted by the dotted lines in FIG. 2, block 202 is optional. In other words, when present, the medical system provides the medical treatment to the patient as described above. When not present, the process 200 may begin at block 204. In other words, the blood monitoring system may simply monitor HCT/HGB concentrations of the patient 10 without performing a medical treatment.

At block 204, the blood monitoring system monitors (e.g., determines and/or obtains) HCT and/or HGB concentrations corresponding to the blood of the patient over a period of time (e.g., during the duration of the dialysis treatment). For example, as mentioned above, the blood monitoring system may use optical techniques to non-invasively measure in real-time the HCT concentrations of the patient. Using the HCT concentrations, the blood monitoring system may determine/calculate the HGB concentrations. Initially, when an OH occurs, the corpuscular blood elements and plasm may be lost in equal proportions and as such, neither the HCT nor HGB concentrations may change immediately. However, a delayed drop in HCT or HGB (e.g., a drop of 1% or 2%) may ensue due to the re-distribution of interstitial fluid into the vascular bed, which dilutes the RBC and results in a drop of HCT and HGB. Accordingly, the blood monitoring system monitors the HCT and/or HGB concentrations to detect a drop of the HCT concentrations (e.g., HCT percentage values) and/or a drop of the HGB concentrations (e.g., HGB levels). The drop of the HCT/HGB concentrations may indicate a potential OH.

In some instances, the monitored HGB and/or HGB concentrations may be measured values. In other instances, the blood monitoring system may apply signal processing to measured values to determine/obtain the monitored HCT and/or HGB concentrations. For instance, the blood monitoring system may use a linear regression over a period of time (e.g., 30 seconds) to determine a hematocrit concentration.

At block 206, based on a change of the HCT and/or HGB concentrations, the blood monitoring system generates a notification indicating a potential OH. For example, the HCT/HGB concentrations may drop due to an OH. The blood monitoring system may compare the drop in the HCT/HGB concentrations with a pre-defined and/or user-defined threshold. Based on the comparison (e.g., based on the drop in HCT/HGB concentrations exceeding the pre-defined threshold), the blood monitoring system may determine the patient is suffering from a potential OH and may generate a notification indicating the potential OH.

In some instances, the HCT/HGB threshold may be specific to the patient. For example, the blood monitoring system may determine the pre-defined threshold based on the patient's blood volume (e.g., either estimated via saline infusion and/or estimated based on the patient's identifying characteristics such as gender, height, weight, and so on) and/or initial HGB/HCT measurements. In some instances, the blood monitoring system may determine this threshold automatically. In other instances, the blood monitoring system may receive feedback from a physician indicating this threshold.

In some variations, this threshold may be pre-defined for non-kidney patients as 10 grams/deciliter (g/dL) for women and 12 g/dL for men. In some instances, the blood monitoring system may determine the patient is suffering from a potential OH based on a time factor and/or a rate of change for the HCT/HGB. For instance, the threshold may be an HGB drop over a period of time such as a 1 to 2 g/dL drop in HGB within 6 hours. Based on detecting the actual HGB drop of the patient exceeds this threshold, the blood monitoring system may determine the patient is suffering from blood loss and provide a notification indicating a potential hemorrhage, hemolysis, and/or other conditions.

At block 208, the blood monitoring system provides the notification indicating the potential OH. In some instances, the blood monitoring system may cause display of the notification such as displaying the notification on the display device 35. In other instances, the notification may be an alarm (e.g., an audio or visual alarm and/or other types of alerts) that notifies the physician/clinician that the patient may be suffering from an OH. Based on the notification, alarm, or alert, the clinician/physician may perform one or more tests to determine whether the potential OH is actually an OH and/or perform one or more additional procedures to treat the OH. For instance, the tests may be a clinical exam, determining whether there is blood within the stool of the patient, blood within the urine, imaging of the patient, and/or specific lab tests.

In some variations, when performing the process 200, the blood monitoring system may determine absolute blood volume (ABV) values and use the ABV values to determine a potential OH. The ABV defines cardiac output (e.g., amount of blood to the tissues) and is generally fairly consistent unless there is an extraneous factor involved (e.g., an OH). Therefore, a drop in ABV (e.g., a drop of 5% or 10%) would raise the likelihood that there is an OH.

To detect an OH using ABV, at block 204, a fluid (e.g., a saline) may be infused and/or injected into a patient. For instance, the medical system may include a pump (e.g., a timed pump) that infuses the saline into the patient (e.g., the patient 10). The blood monitoring system may monitor/obtain the HCT and/or HGB concentrations within the blood of the patient prior to, during, and/or after the infusion of the saline. In some instances, the blood monitoring system may apply signal processing (e.g., linear regression over a period of time) to determine the HCT and/or HGB concentrations. Additionally, in some instances, the pump and the corresponding infusion rate may be controlled by the blood monitoring system or by the medical system.

At block 206, the blood monitoring system may determine/calculate the ABV of the patient based on a change of the hematocrit and/or hemoglobin concentrations. For instance, using Fick's principle, the ABV may be calculated as follows:

$$ABV(pre)*HGB(pre)=(ABV(pre)+\text{Infusion volume})*HGB(post) \quad \text{Eq. (5)}$$

The HGB (pre) is the hemoglobin concentration prior to the infusion of the saline. The HGB (post) is the hemoglobin concentration after the infusion of the saline and after the hemoglobin concentration has stabilized. The Infusion volume is the volume or quantity of the fluid (e.g., saline) infused into the patient by the blood monitoring system. The ABV (pre) is absolute blood volume of the patient prior to infusion of the saline.

Accordingly, based on monitoring the HCT and HGB concentrations at block 204, the blood monitoring system can determine the HGB (pre) and HGB (post) for the patient. Furthermore, the Infusion volume is also known to the clinician and the blood monitoring system (e.g., the blood monitoring system may receive user input indicating the Infusion volume). Accordingly, using Eq. (5), the blood monitoring system may solve for the only unknown, ABV (pre).

The ABV may also be calculated using HCT rather than HGB, which is shown below:

$$ABV(pre)=\text{Infusion volume}*HCT(post)/(HCT(pre)-HCT(post)) \quad \text{Eq. (6)}$$

As shown, the HCT (pre) and HCT (post) are the hematocrit concentrations prior to infusion of the saline and after the infusion of the saline. The Infusion volume is the volume of the fluid infused into the patient.

The blood monitoring system may use either Eq. (5) or Eq. (6) to determine the ABV. Furthermore, this test (e.g., the infusion of the saline into the patient) may be repeated one or more times and a drop in the ABV may indicate a potential OH. In other words, the medical system may infuse saline into the patient two or more times. The blood monitoring system may determine/calculate two or more ABVs based on these infusions. Then, using the two or more ABVs, the blood monitoring system may determine a change (e.g., a decrease) in the ABV. The blood monitoring system may compare this decrease with a pre-defined and/or user-defined threshold and based on the comparison (e.g., based on the decrease in ABV exceeding the pre-defined threshold), the blood monitoring system may determine the patient is suffering from a potential OH and may generate a notification indicating the potential OH.

Afterwards, similar to above, at block 208, the blood monitoring system may provide a notification indicating the potential OH.

Figure 3A:
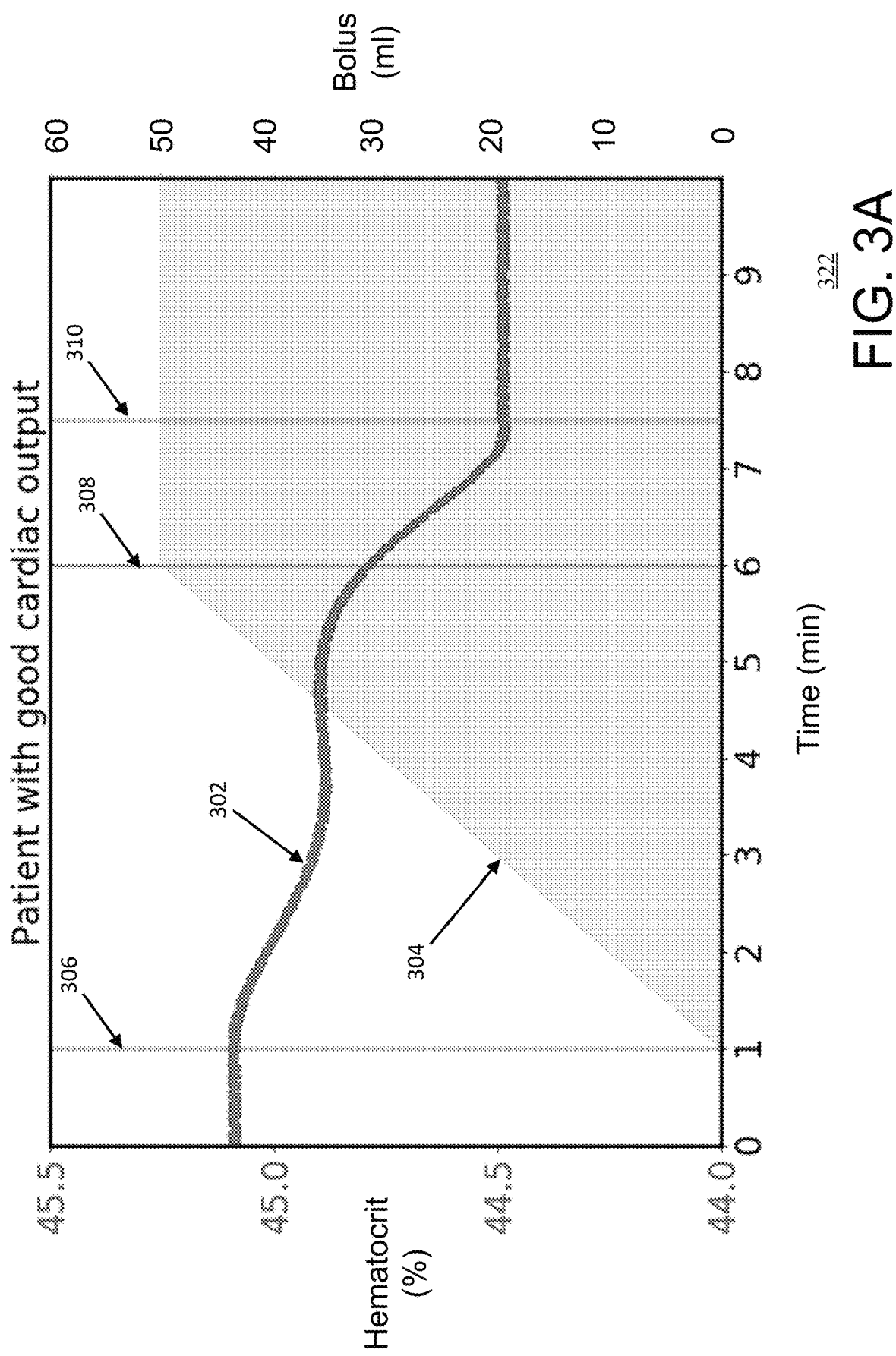
FIGS. 3A and 3B are plots showing changes in hematocrit values for theoretical patients after the patients have been injected with a saline.
Figure 3B:
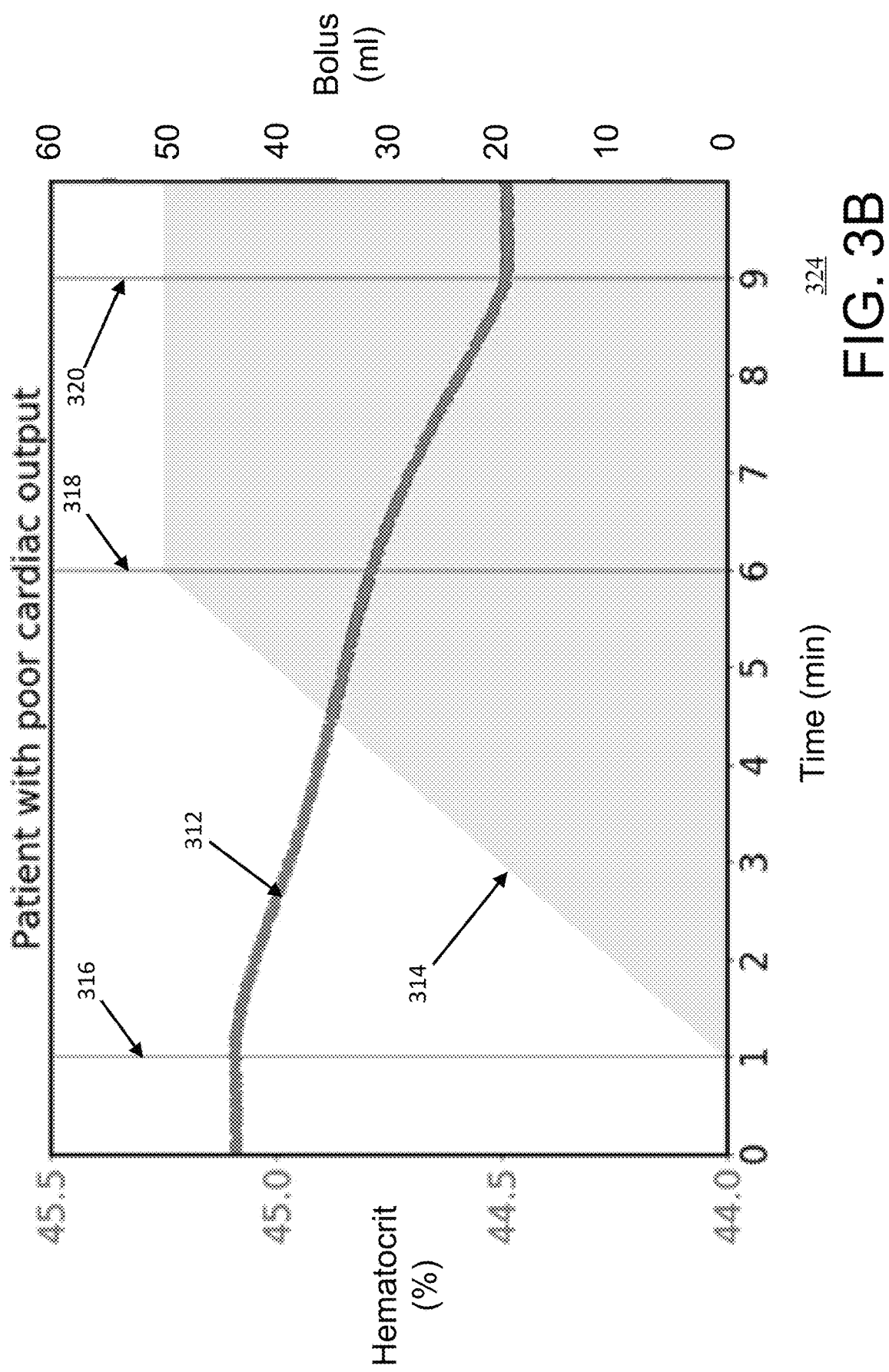

FIGS. 3A and 3B are plots showing changes in hematocrit values for theoretical patients after the patients have been injected with a saline and will describe using the ABV to determine the potential OH in more detail. For instance, FIG. 3A shows a plot 322 of a patient with good cardiac output and the medical system administering an infusion of a saline into the patient. The right-hand side of the plot 322 shows the bolus in milliliters (ml). The bolus is the administration of a discrete amount of saline into the patient. Volume 304 shows the volume of the saline that has been infused into the patient at given times (in minutes). For instance, the medical system uses the timed pump to begin infusing the saline at 1 minute (shown by line 306). From 1-6 minutes, the pump infuses the saline at a constant rate as shown by volume 304. At 6 minutes (shown by line 308), the pump completes the 50 ml infusion of the saline and the volume 304 remains constant at 50 ml. The line 302 shows the HCT concentration (percentage) of the patient. For instance, initially, the HCT concentration 302 is at 45.1%. Then, after the pump begins infusing the saline into the patient, the HCT concentration 302 begins to decrease until it reaches a steady state. As shown, even after the pump has infused the entire infusion volume (50 ml) into the patient, the HCT concentration 302 continues to decrease until around 7.5 minutes (shown by line 310). After that, the HCT concentration 302 reaches a steady state at around 44.5%.

FIG. 3B shows a plot 324 of a patient with poor cardiac output and the medical system administering an infusion of a saline into the patient. For example, similar to FIG. 3A, the volume 314 shows the volume of the saline that has been infused into the patient. For instance, the medical system uses the timed pump to begin infusing the saline at 1 minute (shown by line 316). From 1-6 minutes, the pump infuses the saline at a constant rate as shown by volume 314. At 6 minutes (shown by line 318), the pump completes the 50 ml infusion of the saline and the volume 314 remains constant at 50 ml. Similarly, the line 312 shows the HCT concentration (percentage) of the patient decreasing from 45.1% to 44.5%. However, due to the patient having poor cardiac output, the time for the HCT concentration to reach steady state is at 9 minutes (shown by line 320) rather than 7.5 minutes as shown by FIG. 3A.

In other words, referring to FIGS. 3A and 3B, upon start of the infusion, the HCT concentrations 302 and 312 (and the HGB concentrations as well) will begin to decline. The rate of this decline depends on two factors: the degree of dilution and the rate at which the infusion volume mixes with the blood. This rate is primarily determined by the veno-arterial circulation time, which in turn depends primarily on the cardiac output and the ABV. Therefore, in a given patient, the time between infusion start (at a pre-defined rate) and attainment of a stable (lower) level of HCT (or HGB) is a measure of cardiac output. This time to reach the steady state may be referred to herein as the cardiac equilibration time. In FIG. 3A, the cardiac equilibration time is 6.5 minutes. In FIG. 3B, the cardiac equilibration time is 8 minutes. As such, based on the plots 322 and 324, the blood monitoring system may determine the Infusion volume is 50 ml, the HCT (pre) is 45.1%, and the HCT (post) is 44.5%. Then, using these values, the blood monitoring system may determine the ABV (e.g., around 3710 ml). This test may be repeated to determine whether the ABV has dropped for the patient. Based on comparing this decrease of ABV with a pre-defined threshold, the blood monitoring system may determine whether the decrease in ABV indicates a potential OH.

Additionally, and/or alternatively, a change in the cardiac equilibration time (e.g., the change shown from FIG. 3A to FIG. 3B) may indicate a change in cardiovascular status. The change in cardiovascular status may cause the physician to take one or more steps based on the cause of the worsening cardiac output. For instance, in cases where the patient is fluid overloaded, steps may include increasing the ultrafiltration rate and/or volume. In cases where the patient produces urine, steps may include increasing loop diuretics. In cases where it is a contractility problem, steps may include adding/increasing catecholamine intravenous therapy (IV). In cases where there is a fluid deficit, steps may include giving fluids IV. In cases where the patient is hypoxemic, steps may include giving oxygen, ventilation, and clear airways. In some exemplary embodiments, an intervention or a treatment modification may be triggered automatically by the blood monitoring system in response to the blood monitoring system detecting a change in cardiovascular status and/or a potential OH.

Figure 4:
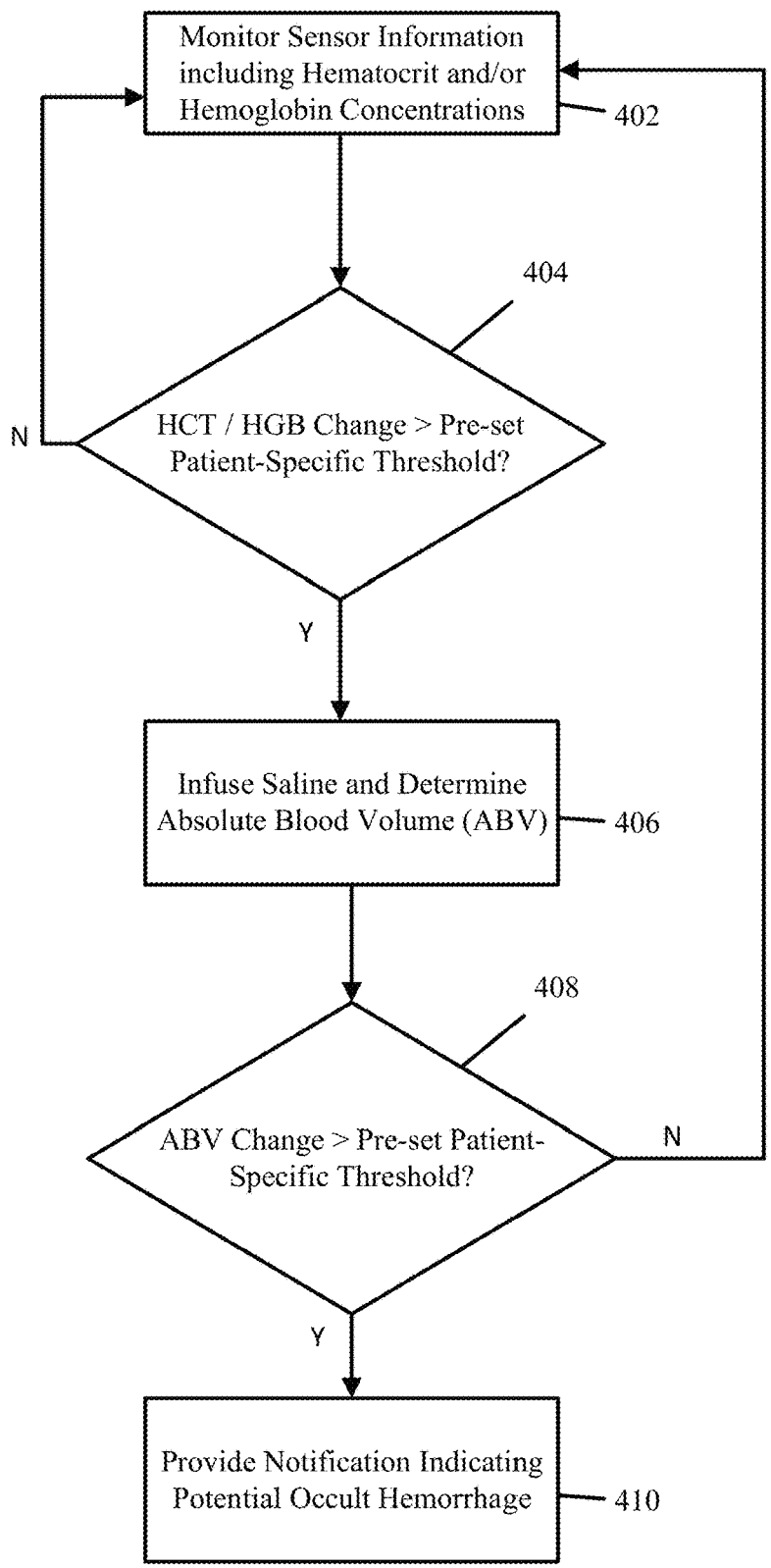
FIG. 4 is a flowchart of another exemplary process for detecting occult hemorrhages using the blood monitoring system.

In some examples, the medical system, which comprises the blood monitoring system, may determine the potential OH based on using a combination of monitoring for a change of the HCT/HGB concentrations as well as infusing the saline into the patient to determine the ABVs. FIG. 4 is another flowchart of an exemplary process 400 for detecting OHs using both the change in HCT/HGB concentrations as well as determining the ABVs based on infusing the saline. For example, similar to block 204, at block 402, the blood monitoring system monitors sensor information including HCT and HGB concentrations. At block 404, the blood monitoring system determines whether the HCT/HGB change is greater than a pre-set patient-specific threshold for HCT or HGB. If yes, then the process 400 moves to block 406. If no, then the process 400 moves back to block 402.

At block 406 and as described above, the medical system uses the pump to infuse saline into the patient and determines the ABV. The medical system may perform this two or more times. At block 408, the blood monitoring system determines whether the change in ABV is greater than a pre-set patient specific threshold for ABV. If no, the process 400 moves back to 402. If yes, the process 400 moves to block 410. At block 410 and similar to block 206 and 208, the blood monitoring system provides a notification indicating a potential OH.

In some instances, the ABV threshold may be based on the patient (e.g., may be based on initial HGB/HCT measurements and/or the patient's identifying characteristics). The blood monitoring system may determine this threshold automatically and/or based on feedback from a physician. The change in ABV indicates the blood volume loss. In some examples, the minimal clinically relevant blood loss depends on the starting point for the patient. In a healthy adult patient, the patient typically has about 70 milliliters of blood per kilogram (ml/kg) of body weight. As such, a blood loss of less than 500 milliliters (mL) might not be concerning (e.g., a loss of approximately 10% of ABV). However, a 15-25% ABV loss may be concerning and a 30-40% ABV loss may be lethal. Therefore, in some variations, the threshold may be set such that a 10% loss or 15% loss of ABV would trigger the notification indicating the potential OH.

In other words, in some instances, the medical system may use a two-tiered approach that combines the two procedures described above to determine whether the patient is suffering from a potential OH. The first tier may be to monitor the HCT and HGB over a period of time to detect an unexplained drop in HCT/HGB. After detecting the drop, the second tier may be to infuse the patient with saline to determine the ABV. Based on the drop in HCT/HGB and the change in ABV, the medical system may determine whether the patient is suffering from an OH. By using this two-tiered approach, the medical system may be able to prevent unnecessary infusions of saline as well as provide sufficient accuracy in detecting an OH.

FIG. 5 is a block diagram of an exemplary network environment in which a hemodialysis system communicates with an electronic health records (EHR) system to provide HCT, HGB, and/or ABV data to the EHR system. The network environment includes one or more dialysis clinics (including a respective dialysis clinic 510) and an EHR system 530.

The dialysis clinic 510 includes one or more hemodialysis systems used to provide hemodialysis treatment to one or more patients (including a respective patient 511 and a respective hemodialysis system 512). Each of the hemodialysis systems is in communication with a gateway device 513, for example, via a wired connection (e.g., an Ethernet RJ-45 connection or a fiber optic connection) or a wireless connection (e.g., via Bluetooth or WiFi). For example, a display device or a sensor device of an optical blood monitoring system of each of the hemodialysis systems may include a communications interface and corresponding communications equipment for communicating with the gateway device via the wired or wireless connection. The gateway device 513 is configured to communicate with an EHR system 530 over one or more networks (such as via a private computing network, via a public computing network such as the Internet, and/or via a mobile communications network). The EHR system 530 includes, for example, at least one application server 531 and at least one database 532 connected to the at least one application server 531. The EHR system 330 is configured, among other things, to store patient health information (e.g., pertaining to patient 511 and other patients being treated at the one or more dialysis clinics) in the at least one database 532 and to process and respond to requests for electronic health information via the at least one application server 531. The EHR system 530 receives patient health information from various sources, including the one or more dialysis clinics, and the EHR system 530 may be configured to communicate with the various sources over one or more networks (such as via a private computing network, via a public computing network such as the Internet, and/or via a mobile communications network).

In accordance with exemplary embodiments of the present application, as shown in FIG. 5, the dialysis clinic 510 may further provide HCT, HGB, and/or ABV data corresponding to patient 511 to the EHR system 530 for storage and/or for further analysis or processing. Data may be sent to the EHR system 530 in real-time or in batches, and the EHR system 530 may maintain historical HCT, HGB, and/or ABV data for a plurality of patients in the at least one database 532. Further, based on the historical data for a particular patient, the EHR system (or another system in communication with the EHR system) may detect a potential chronic issue for the patient that evolves relatively slowly (e.g., over the course of multiple treatments or several months or even years).

The EHR system 530 (or another system in communication with the dialysis clinic 510) may be configured for remote monitoring of dialysis treatments being performed at the dialysis clinic 510. Further, the EHR system 530 (or another system in communication with the EHR system) may utilize aggregated HCT, HGB, and/or ABV data for further analysis, for example, in connection with patient outcomes. In an exemplary implementation, the EHR system 530 may be configured to provide a correlation analysis with regard to diagnosed cases of OH and collected HCT, HGB, and/or ABV data.

It will be appreciated that the network environment depicted in FIG. 5 is merely exemplary, and that the principles discussed herein are also applicable to other types of network configurations, entities, and equipment.

It will be appreciated that although some of the exemplary embodiments discussed above include one or more dialysis machines, the present application is not limited thereto and other types of medical systems may be used to detect a potential OH. For example, another type of medical system may monitor HGB/HCT concentrations. Additionally, the medical system may include a pump to infuse the blood with saline and determine the ABV of the patient. Using the HGB, HCT, and/or ABV, the medical system may determine a potential OH. Additionally, and/or alternatively, the medical system may include a blood monitoring system that is capable of obtaining non-invasive and/or transcutaneous blood measurements (e.g., transcutaneous HCT and/or HGB measurements).

Exemplary embodiments of the present application provide for improved detection of OH using HGB concentrations, HCT concentrations, and/or the ABV of the patient. By using this detection method, the present application is able to non-invasively detect OH in a timelier manner, and patient safety and outcomes may be improved.

It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

All references, including publications, patent applications, and patents, cited herein are hereby incorporated by reference to the same extent as if each reference were individually and specifically indicated to be incorporated by reference and were set forth in its entirety herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method for detecting occult hemorrhages, comprising:

obtaining, by a medical system comprising an optical blood monitoring system that uses one or more light intensities, first sensor information indicating a first hematocrit concentration prior to infusing a first saline solution into a bloodstream of a patient;

infusing, by the medical system, the first saline solution into the bloodstream of the patient;

obtaining, by the medical system and using the optical blood monitoring system, second sensor information indicating a second hematocrit concentration after infusing the first saline solution into the bloodstream;

determining, by the medical system, an infusion volume of the first saline solution that is infused into the bloodstream of the patient;

determining, by the medical system, a first absolute blood volume corresponding to an amount of cardiac output of blood to tissues of the patient, wherein determining the first absolute blood volume is based on using the following equation:

ABV(pre)=Infusion volume*HCT(post)/(HCT(pre)−HCT(post)), where ABV (pre) is the first absolute blood volume, HCT (post) is the second hematocrit concentration, HCT (pre) is the first hematocrit concentration, and Infusion volume is the infusion volume of the first saline solution;

infusing, by the medical system, a second saline solution into the bloodstream of the patient;

determining, by the medical system, a second absolute blood volume based on infusing the second saline solution;

determining, by the medical system, a change between the first absolute blood volume and the second absolute blood volume;

generating, by the medical system, a notification indicating a potential occult hemorrhage based on comparing the change between the first absolute blood volume and the second absolute blood volume with a pre-defined absolute blood volume threshold; and providing, by the medical system, the notification indicating the potential occult hemorrhage.

2. The method of claim 1, wherein the second hematocrit concentration is obtained based on a hematocrit concentration of the patient reaching a steady-state after infusing the first saline solution into the bloodstream of the patient.

3. A method for detecting occult hemorrhages, comprising:

obtaining, by an optical blood monitoring system, of a medical system, that uses one or more light intensities, first sensor information indicating a detected hematocrit concentration or a detected hemoglobin concentration of a patient;

comparing, by the optical blood monitoring system, the detected hematocrit concentration or the detected hemoglobin concentration with a pre-defined hematocrit or hemoglobin threshold, wherein the pre-defined hematocrit or hemoglobin threshold is patient-specific;

in response to the detected hematocrit concentration or the detected hemoglobin concentration exceeding the pre-defined hematocrit or hemoglobin threshold, infusing a first saline solution into a bloodstream of the patient;

obtaining, by the optical blood monitoring system, second sensor information indicating a second hematocrit concentration after infusing the first saline solution into the bloodstream;

obtaining an infusion volume associated with the first saline solution;

determining a first absolute blood volume based on using the following equation:

ABV(pre)=Infusion volume*HCT(post)/(HCT(pre)−HCT(post)), where ABV (pre) is the first absolute blood volume, HCT (post) is the second hematocrit concentration, HCT (pre) is the detected hematocrit concentration or a hematocrit concentration associated with the detected hemoglobin concentration, and Infusion volume is the infusion volume associated with the first saline solution;

generating, by the optical blood monitoring system, a notification indicating a potential occult hemorrhage based on the first absolute blood volume and a pre-defined absolute blood volume threshold; and providing, by the optical blood monitoring system, the notification indicating the potential occult hemorrhage.

4. The method of claim 3, wherein the pre-defined hematocrit or hemoglobin threshold is a patient-specific hematocrit threshold, and wherein infusing the first saline solution is in response to the detected hematocrit concentration exceeding the patient-specific hematocrit threshold.

5. The method of claim 3, wherein the first sensor information indicates the detected hematocrit concentration, and wherein the method further comprises:

determining the detected hemoglobin concentration based on the detected hematocrit concentration, wherein the pre-defined hematocrit or hemoglobin threshold is a patient-specific hemoglobin threshold, and wherein infusing the first saline solution is in response to the detected hemoglobin concentration exceeding the patient-specific hemoglobin threshold.

6. The method of claim 3, wherein obtaining the first sensor information comprises obtaining the detected hematocrit concentration prior to infusing the first saline solution into the bloodstream, and wherein the second hematocrit concentration is associated with a hematocrit concentration of the patient reaching a steady-state after infusing the first saline solution into the bloodstream.

7. The method of claim 3, wherein the pre-defined hematocrit or hemoglobin threshold is a patient-specific hemoglobin threshold, and wherein infusing the first saline solution comprises:

determining the detected hemoglobin concentration based on the detected hematocrit concentration;

comparing the detected hemoglobin concentration with the patient-specific hemoglobin threshold;

based on the detected hemoglobin concentration exceeding the patient-specific hemoglobin threshold:

infusing, by the optical blood monitoring system, the first saline solution into the bloodstream of the patient at a first instance in time.

8. The method of claim 3, wherein the medical system is a dialysis system comprising the optical blood monitoring system and a dialysis machine, and wherein the method further comprises:

providing, by the dialysis machine, dialysis treatment to the patient.

9. A medical system, comprising:

an optical blood monitoring system that uses one or more light intensities;

a pump, one or more processors; and a non-transitory computer-readable medium having processor-executable instructions stored thereon, wherein the processor-executable instructions, when executed by the one or more processors, facilitate:

obtaining, using the optical blood monitoring system, a first hematocrit concentration prior to using the pump to infuse a first saline solution into a bloodstream of a patient;

using the pump to infuse the first saline solution into the bloodstream of the patient;

obtaining, using the optical blood monitoring system, a second hematocrit concentration after using the pump to infuse the first saline solution into the bloodstream of the patient;

determining an infusion volume of the first saline solution that is infused into the bloodstream of the patient;

determining a first absolute blood volume based on using the following equation:

ABV(pre)=Infusion volume*HCT(post)/(HCT(pre)−HCT(post)), where ABV (pre) is the first absolute blood volume, HCT (post) is the second hematocrit concentration, HCT (pre) is the first hematocrit concentration, and Infusion volume is the infusion volume of the first saline solution;

determining a second absolute blood volume based on another infusion of a second saline solution into the bloodstream of the patient;

determining a change between the first absolute blood volume and the second absolute blood volume;

generating a notification indicating a potential occult hemorrhage based on comparing the change between the first absolute blood volume and the second absolute blood volume with a pre-defined threshold, wherein the pre-defined threshold is patient-specific; and providing the notification indicating the potential occult hemorrhage.

10. The medical system of claim 9, wherein the second hematocrit concentration is obtained based on a hematocrit concentration of the patient reaching a steady-state after infusing the first saline solution into the bloodstream of the patient.

* * * * *